United States Patent
Hayama et al.

(10) Patent No.: US 11,241,416 B2
(45) Date of Patent: *Feb. 8, 2022

(54) EDARAVONE SUSPENSION FOR ORAL ADMINISTRATION

(71) Applicant: MITSUBISHI TANABE PHARMA CORPORATION, Osaka (JP)

(72) Inventors: Tetsuo Hayama, Osaka (JP); Tomohiro Takahashi, Osaka (JP); Tomoyuki Omura, Osaka (JP); Kouji Hayashi, Osaka (JP); Munetomo Matsuda, Osaka (JP); Tadashi Miyazawa, Osaka (JP)

(73) Assignee: MITSUBISHI TANABE PHARMA CORPORATION, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/213,501

(22) Filed: Mar. 26, 2021

(65) Prior Publication Data
US 2021/0212990 A1 Jul. 15, 2021

Related U.S. Application Data

(63) Continuation of application No. 16/872,741, filed on May 12, 2020, now Pat. No. 10,987,341, which is a (Continued)

(30) Foreign Application Priority Data
Nov. 2, 2018 (JP) .............................. JP2018-207646

(51) Int. Cl.
*A61K 31/4152* (2006.01)
*A61K 9/16* (2006.01)
(Continued)

(52) U.S. Cl.
CPC ........ *A61K 31/4152* (2013.01); *A61K 9/0053* (2013.01); *A61K 9/16* (2013.01);
(Continued)

(58) Field of Classification Search
None
See application file for complete search history.

(56) References Cited

U.S. PATENT DOCUMENTS 10,987,341 B2 * 4/2021 Hayama ............. A61K 31/4152
2019/0083490 A1 3/2019 Saito

FOREIGN PATENT DOCUMENTS

JP H05-031523 B2 5/1993
JP H11-020463 A 2/1999
(Continued)

OTHER PUBLICATIONS

Rong et al., "Hydroxypropyl-Sulfobutyl-β-Cyclodextrin Improves the Oral Bioavailability of Edaravone by Modulating Drug Efflux Pump of Enterocytes", Journal of Pharmaceutical Sciences 103: pp. 730-742, 2014.
(Continued)

*Primary Examiner* — Lakshmi S Channavajjala
(74) *Attorney, Agent, or Firm* — Oblon, McClelland, Maier & Neustadt, L.L.P.

(57) ABSTRACT

An edaravone suspension for human oral administration includes edaravone particles, a dispersant, and water.

20 Claims, 1 Drawing Sheet

Related U.S. Application Data continuation of application No. PCT/JP2019/043013, filed on Nov. 1, 2019.

(51) Int. Cl.
    *A61P 21/00*     (2006.01)
    *A61K 9/00*     (2006.01)
    *A61K 47/32*     (2006.01)
    *A61K 47/36*     (2006.01)

(52) U.S. Cl.
    CPC ............. *A61K 47/32* (2013.01); *A61K 47/36* (2013.01); *A61P 21/00* (2018.01)

(56) References Cited

FOREIGN PATENT DOCUMENTS

| | | |
|---|---|---|
| JP | 2004-091441 A | 3/2004 |
| JP | 3758164 B2 | 3/2006 |
| JP | 2012-056950 A | 3/2012 |
| JP | 2014-177415 A | 9/2014 |
| WO | WO 2018/133957 A1 | 7/2018 |
| WO | WO 2018/134243 A1 | 7/2018 |
| WO | WO 2021/009775 A1 | 1/2021 |

OTHER PUBLICATIONS

Parikh, et al. "Development of a novel oral delivery system of edaravone for enhancing bioavailability", International Journal of Pharmaceutics 2016, 515(1), pp. 490-500.

Parikh, et al. "Lipid-based nanosystem of edaravone: development, optimization, characterization and in viiro/in vivo evaluation", Drug Delivery, 2017, 24(1), pp. 962-978.

Li et al., "Phase I Clinical Study of Edaravone in Healthy Chinese Volunteers", Drugs R D, 2012, 12(2), pp. 65-70.

International Search Report dated Dec. 24, 2019 in PCT/JP2019/043013, filed Nov. 1, 2019, 2 pages.

\* cited by examiner

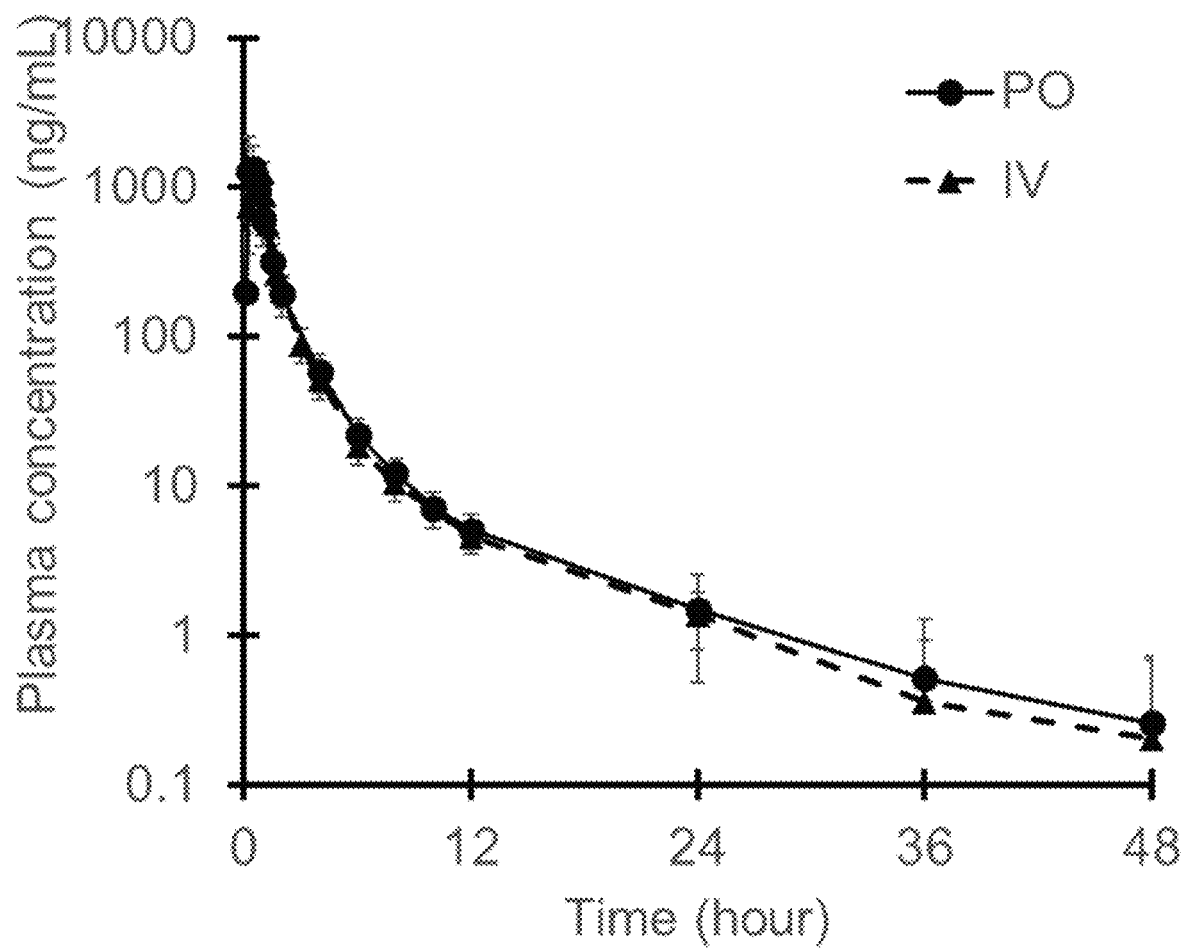

EDARAVONE SUSPENSION FOR ORAL ADMINISTRATION

CROSS-REFERENCE TO RELATED APPLICATIONS

The present application is a continuation of U.S. application Ser. No. 16/872,741, filed May 12, 2020, which claims the benefit of priority to International Application No. PCT/JP2019/043013, filed Nov. 1, 2019, which is based upon and claims the benefit of priority to Japanese Application No. 2018-207646, filed Nov. 2, 2018. The entire contents of these applications are incorporated herein by reference.

BACKGROUND OF THE INVENTION

Field of the Invention

The present invention relates to an edaravone suspension for oral administration, and relates to a kit for preparing the edaravone suspension for oral administration.

Description of Background Art

Edaravone is 3-methyl-1-phenyl-2-pyrazolin-5-one (see formula below)

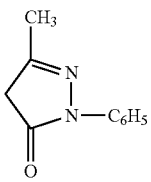

Chemical Formula 1 and has its medicinal use as an ALS (amyotrophic lateral sclerosis) therapeutic agent in addition to being a brain function normalizing agent (Japanese Patent Publication No. H5-31523 and Japanese Patent No. 3758164).

ALS as one type of motor neuron disease is an intractable disease that leads to respiratory failure from initial symptoms such as weakness in hands, movement disorders with fingers and fascicular contraction in upper limbs, through symptoms such as amyotrophia and/or muscular weakness, bulbar paralysis and fascicular contraction in muscles. ALS is divided into upper limb, bulbar, lower limb and mixed types, depending on a site of onset. In all of these types, as symptoms progress, a systemic muscle group is affected. Causal factors of ALS have not yet been sufficiently elucidated. The following hypotheses have been proposed as main causal factors of ALS: (1) autoimmune theory (appearance of an autoantibody against a Ca channel); (2) excessive excitatory amino acid and/or toxication theory (an increase in extracellular glutamic acid and transport disorders of glutamic acid); (3) oxidative stress disorder theory (Cu/Zn superoxide dismutase (SOD) genetic abnormality and nerve cell damage caused by free radicals); (4) cytoskeleton disorder theory (accumulation of neurofilament in motor nerve cells and appearance of inclusion bodies); and (5) deficiency of neurotrophic factors.

The entire contents of these publications are incorporated herein by reference.

SUMMARY OF THE INVENTION

According to one aspect of the present invention, an edaravone suspension for human oral administration includes edaravone particles, a dispersant, and water.

According to another aspect of the present invention, an ALS therapeutic agent includes an edaravone suspension including edaravone particles, a dispersant, and water such that the edaravone suspension has a dose of a drug product per one oral administration in a range of 1 to 20 mL, and the dose contains edaravone in a range of 50 to 210 mg.

According to yet another aspect of the present invention, a kit for preparing an edaravone suspension for human oral administration includes a solid composition including edaravone particles, and a dispersant solution.

According to still another aspect of the present invention, an edaravone suspension is formulated such that when edaravone in the edaravone suspension is in a range of 90 to 120 mg, edaravone in a plasma exhibits a mean Cmax in a range of 500 to 2500 ng/mL and a mean $AUC_{0-\infty}$ in a range of 1000 to 2500 h*ng/mL when the edaravone suspension is orally administered to a human.

According to still another aspect of the present invention, an edaravone suspension is formulated such that when edaravone in the edaravone suspension is in a range of 90 to 120 mg, and a crossover study is performed such that the edaravone suspension is orally administered to a human and that an edaravone injection is used as a control drug product, a lower limit of a 90% confidence interval of a ratio of a Cmax geometric mean value with respect to the control drug product and a lower limit of a 90% confidence interval of a ratio of an $AUC_{0-\infty}$ geometric mean value with respect to the control drug product both exceed 0.8.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGURE is a graph showing the PK profile of unchanged edaravone in plasma at the time of administration of suspension described in Example 26 and the PK profile of unchanged edaravone in plasma at the time of administration of the edaravone injection, where PO is the suspension, and IV is the injection.

DETAILED DESCRIPTION OF THE EMBODIMENTS

Embodiments will now be described with reference to the accompanying drawings, wherein like reference numerals designate corresponding or identical elements throughout the various drawings.

In the following, edaravone suspensions for oral administration of the present invention and a kit for preparing an edaravone suspension for oral administration according to an embodiment of the present invention are described in detail. All publications cited in the present specification are incorporated by reference in the present specification.

Further, in the present specification, "% (w/v)" means mass % with respect to a volume of a suspension unless otherwise specified, and a numerical range indicated using "–" indicates a range including numerical values before and after "–" as minimum and maximum values, respectively.

A suspension for human oral administration according to an embodiment of the present invention contains edaravone particles, a dispersant and water. As a result, the suspension reduces burden on ALS patients and caregivers, and achieves an ALS therapeutic effect equivalent to that of an injection.

A suspension according to an embodiment of the present invention may further contain a thickening agent when necessary.

As a result, even patients with dysphagia can easily drink without a risk of aspiration, and a dispersion state of the edaravone particles can be maintained for a longer time. Further, by containing a thickening agent, when the suspension is administered to humans, variation in drug concentration in blood among patients can be greatly reduced, and a more stable drug effect can be expected.

Edaravone can be synthesized by a person skilled in the art, for example, using a method described in Japanese Patent Publication No. H5-31523.

The edaravone particles contained in a suspension according to an embodiment of the present invention are solid particles containing edaravone, and may be formed of edaravone alone or may contain other components. Edaravone may be in a crystalline state or an amorphous state.

Particle sizes of the edaravone particles in the suspension are not particularly limited. However, from perspectives such as maintaining a stable dispersed state in the suspension, rapid in-body absorption and a smooth feeling when the suspension is taken, preferably, a D50 particle size (volume-based cumulative 50% particle size) is in a range of 10 µm-100 µm, and a D90 particle size (volume-based cumulative 90% particle size) is in a range of 50 µm-300 µm; and, more preferably, the D50 particle size is in a range of 20 µm-80 µm, and the D90 particle size is in a range of 100 µm-250 µm. In the present invention, the cumulative 50% particle size and the cumulative 90% particle size are volume-based particle sizes.

Particle size distribution of the edaravone particles in the suspension is measured using a laser diffraction particle size distribution device (Sympatec/HELOS & CUVETTE) by dispersing a part of the suspension in a dispersion medium for measurement (edaravone saturated aqueous solution).

A concentration (blending amount) of the edaravone particles blended in a suspension according to an embodiment of the present invention can be appropriately adjusted according to an optimal dose of edaravone and an amount of the suspension provided to an ALS patient (one dose, a daily dose, a weekly dose, a 10-day dose, and the like). However, an amount that allows a form as a suspension to be retained is appropriate. When the edaravone particles are formed of only edaravone, the concentration of the edaravone particles may be 2 mg/mL or more which is equal to or higher than a saturation solubility of edaravone with respect to a dispersion medium (for example, water), and is preferably 0.06% (w/v)-36% (w/v), more preferably 0.5% (w/v)-36% (w/v), or 0.5% (w/v)-20% (w/v), even more preferably 1% (w/v)-20% (w/v), or 1% (w/v)-10% (w/v), and most preferably 1% (w/v)-5% (w/v).

The suspension of the present invention contains a dispersant. As a result, the edaravone particles in the suspension of the present invention are in a well dispersed state, and even when the edaravone particles have settled after a long period of time of storage, the edaravone particles can be quickly redispersed by shaking (for example, manual or mechanical shaking). A behavior of redispersion can be confirmed visually or using a spectroscopic method (for example, using a laser diffraction particle size distribution device).

As the dispersant, any dispersant that allows the edaravone particles to be well dispersed in water without causing the edaravone particles to form secondary agglomerates may be used. An example of such a dispersant is a dispersant exhibiting a transmission scattering light intensity of 1% or more. Here, "1% or more" means a range of 1%-100%.

A dispersant exhibiting a transmission scattering light intensity of X % or more means a dispersant for which, when a transmission scattering light intensity ($\Delta T$ %) just below a surface of a liquid obtained by mixing 40 mL of a 0.1% (w/v) aqueous solution of the dispersant and 840 mg of edaravone is measured, the transmission scattering light intensity is X % or more. For example, a dispersant exhibiting a transmission scattering light intensity of 1% or more means a dispersant for which, when a transmission scattering light intensity ($\Delta T$ %) just below a surface of a liquid obtained by mixing 40 mL of a 0.1% (w/v) aqueous solution of the dispersant and 840 mg of edaravone (D50: 37 µm, D90: 143 µm) and stirring the mixture with a stirrer for 30 minutes or more is measured, the transmission scattering light intensity is 1% or more. Further, here, the transmission scattering light intensity means a value obtained after 10 minutes after starting a measurement of a transmission scattering light intensity, the measurement being performed by filling 20 mL of the above liquid in a cylindrical sample bottle (inner diameter: 25 mm×outer diameter: 27.5 mm×height: 72 mm) and by measuring the transmission scattering light intensity at a height of 39-40 mm of the sample bottle using a TURBISCAN Tower (manufactured Formulaction) (25° C.).

Examples of a dispersant exhibiting a transmission scattering light intensity of 1% or more include polyvinyl alcohol, sucrose fatty acid ester, polysorbate, methylcellulose, and hypromellose.

Further, as the dispersant, a dispersant exhibiting a contact angle of 80 degrees or less can also be suitably used. Here, "80 degrees or less" means a range of 0-80 degrees. A dispersant exhibiting a contact angle of 80 degrees or less means a dispersant for which, when a droplet of edaravone saturated aqueous solution containing a 0.1% (w/v) dispersant dissolved therein is dropped on an edaravone tablet, an angle (contact angle) formed between a tangent of the droplet and a surface of the edaravone tablet is 80 degrees or less. Here, the edaravone tablet refers to an edaravone tablet obtained by compression-molding 120 mg of edaravone (D50: 37 µm, D90: 143 µm) in a flat punch having a diameter of 8 mm at a tableting pressure of 800 kg, and measurement of the contact angle refers to a case where the contact angle is measured using a contact angle measuring device (CAX-150 manufactured by Kyowa Interface Science) under the following conditions.

Syringe used: glass, 1 mL
Needle: 23 gauge
Liquid volume: 1 µL
Measurement time: after 3.1 seconds Examples of a dispersant exhibiting a contact angle of 80 degrees or less include polyvinyl alcohol, sucrose fatty acid ester, polysorbate, hypromellose, and the like.

Specific examples of a preferred dispersant are one or more selected from a group of polyvinyl alcohol, sucrose fatty acid ester, polysorbate, methylcellulose and hypromellose. Particularly preferably, the dispersant is one or two selected from a group of polyvinyl alcohol and methylcellulose, and most preferably, the dispersant is polyvinyl alcohol.

As the polyvinyl alcohol, a polyvinyl alcohol is preferred that has a saponification degree of 86.5-89.0, of which a kinematic viscosity of a 4% aqueous solution is in a range of 3 mm$^2$/s-55.7 mm$^2$/s at 20° C., and that is recommended as a pharmaceutical additive. However, the polyvinyl alcohol is not limited to this. For example, Gohsenol EG-03P, EG-05P, EG-05PW, EG-18P, EG-22P, EG-30P, EG-30PW, EG-40P, EG-40PW, and EG-48P, commercially available from Nippon Synthetic Chemical Industry Co., Ltd., can be used.

These dispersants may each be independently used, or two or more of these dispersants may be used in combination.

A blending amount of the dispersant may be selected in a range that allows the edaravone particles to be dispersed and does not adversely affect manufacturability, and is usually in a range of 0.001% (w/v)-1.0% (w/v), preferably 0.005% (w/v)-0.5% (w/v), and most preferably 0.01% (w/v)-0.1% (w/v).

In a suspension according to an embodiment of the present invention, in order for the edaravone particles to maintain a well dispersed state for a long period of time, a thickening agent may be blended. By containing a thickening agent, an effect is achieved that the suspension is easily swallowed without a risk of aspiration even for patients with dysphagia and, when being administered to humans, variation in drug concentration in blood among patients is greatly reduced, and a more stable drug effect can be expected.

As the thickening agent, a pharmaceutically known thickening agent can be used. Specifically, for example, carmellose sodium, dextrin, tragacanth powder, xanthan gum, and the like can be used. From a perspective of storage stability of edaravone, tragacanth powder and xanthan gum are preferable, and xanthan gum is most preferable.

These thickening agents may each be independently used, or two or more of these thickening agents may be used in combination.

A larger blending amount of the thickening agent allows a dispersed state to be maintained for a longer period of time. However, when the blending amount is too large, viscosity is strong and manufacturability deteriorates, and a drug product becomes difficult to be swallowed and redispersibility of settled particles after a long period of time of storage also deteriorates, and thus, it is unfavorable. For example, the thickening agent is xanthan gum, the blending amount of the thickening agent may be 0.1% (w/v)-1.2% (w/v), and preferably 0.2% (w/v)-1.0% (w/v), and most preferably 0.3% (w/v)-0.5% (w/v).

Blending a thickening agent can impart viscosity to the suspension, allows even a patient with dysphagia to easily drink the suspension, and can prevent aspiration, and thus is favorable. The viscosity of such a suspension may be in a range not exceeding 1750 mPa·s, preferably in a range of 50 mPa·s-1750 mPa·s, and most preferably in a range of 150 mPa·s-900 mPa·s.

The blending amount of the thickening agent is not limited to the above description, and can be adjusted as appropriate such that the above viscosity is achieved.

Further, blending the thickening agent achieves an unexpected effect that, when the suspension is administered to patients, variation in edaravone concentration transition in blood among the patients can be minimized, and thus, a stable drug effect can be expected for all the patients.

In a suspension for oral administration according to an embodiment of the present invention, a sweetener can be blended for purposes of adjusting taste of the suspension as a drug product for oral administration and delaying settling of the edaravone particles by increasing a solution density of the suspension. Among sweeteners, sugar can increase a blending ratio as compared to other additives and can contribute to increasing a solution density. Further, dissolving sugar allows a solution density to be brought close to that of the particles, and can contribute to suppressing a settling speed of the particles.

The density of the suspension is desirably close to that of the edaravone particles, and is in a range equal to or exceeding the density of water, and is preferably in a rage of 1 g/mL-1.5 g/mL, and most preferably in a range of 1.05 g/mL-1.2 g/mL.

Examples of the sweetener include sugars, artificial sweeteners, and non-sugar sweeteners. Specific examples of sugars include mannitol, sorbitol, xylitol, maltitol, erythritol, sucrose, trehalose, lactose, maltose, glucose, glycerin, and the like. Specific examples of artificial sweeteners include sucralose, aspartame, acesulfame potassium, saccharin, and the like. Specific examples of non-sugar sweeteners include thaumatin, stevia extract, and the like. Among these, sorbitol, xylitol, or sucrose is preferable, sorbitol, or sucrose is more preferable, and sorbitol is most preferable.

These sweeteners may each be independently used, or two or more of these sweeteners may be used in combination.

A blending amount of a sweetener can be adjusted as appropriate in consideration of preference of a recipient and suppression of settling of the particles. However, a blending amount of sorbitol is 5% (w/v)-70% (w/v), preferably 10% (w/v)-60% (w/v), and more preferably 20% (w/v)-50% (w/v).

Edaravone as a pharmaceutical ingredient has a property of being susceptible to oxidation by dissolved oxygen in a liquid, and thus, it is preferable to blend a stabilizer in a suspension according to an embodiment of the present invention. Examples of such a stabilizer include antioxidants such as sulfites, bisulfites, and pyrosulfites, cysteines, methionines, polyethylene glycol, polyoxyethylene polyoxypropylene glycol, EDTA, and the like. Particularly preferred are stabilizers described in Japanese Patent Publication No. H7-121861. That is, the stabilizers are one or more antioxidants selected from sulfites, bisulfites and pyrosulfites, and stabilizers selected from cysteines.

Examples of sulphites include sodium sulfite ($Na_2SO_3$), potassium sulfite ($K_2SO_3$), and calcium sulfite ($CaSO_3$). Examples of bisulfites include sodium bisulfite ($NaHSO_3$), potassium bisulfite ($KHSO_3$), and ammonium bisulfite ($NH_4HSO_3$). Examples of pyrosulfites include sodium pyrosulfite ($Na_2S_2O_5$) and potassium pyrosulfite ($K_2S_2O_5$). Further, examples of cysteines include L-cysteine, DL-cysteine, N-acetylcysteine, hydrochlorides thereof, and the like. Most preferably, as an antioxidant, sodium bisulfite can be used, and as a cysteine, L-cysteine hydrochloride can be used.

An additive amount of the antioxidant is preferably 0.001% (w/v)-0.5% (w/v), and particularly preferably 0.01% (w/v)-0.2% (w/v), and an additive amount of the cysteine is preferably 0.005% (w/v)-0.5% (w/v), and particularly preferably 0.01% (w/v)-0.2% (w/v).

Further, since oxidation of edaravone is accelerated at a pH of 2.5 or lower and at a pH of 6.0 or higher, a pH regulator is preferably blended in a suspension according to an embodiment of the present invention. The pH regulator can be used in an amount such that the pH of the suspension is adjusted to a range of 2.5-6.0, and preferably to a range 3.0-4.5. Either a base or an acid can be used to adjust the pH to a desired value. When it is necessary to lower the pH, an acidic pH regulator (for example, a hydrochloric acid, a phosphoric acid, an acetic acid, a citric acid, a tartaric acid, or the like, preferably a phosphoric acid) can be used. When it is necessary to raise the pH, a basic pH regulator (for example, a sodium hydroxide, a potassium hydroxide, a calcium carbonate, a magnesium oxide, a magnesium hydroxide, or the like, preferably a sodium hydroxide) can be used.

In a suspension according to an embodiment of the present invention, when necessary, pharmaceutically acceptable drug product additives such as fragrances, preservatives and antifoaming agents may be further blended.

Fragrances of various flavors such as citrus flavors (such as orange, lemon, and grapefruit), peach, grape, vanilla, soda, and berry flavors (such as strawberry, cranberry, and blueberry) can be used. A preferred blending amount of a fragrance is, for example, 0.05% (w/v)-0.2% (w/v).

Examples of antifoaming agents include simethicone emulsions, fatty acid esters, polysorbates, ethanol, and the like. A blending amount of an antifoaming agent is, for example, 0.01% (w/v)-0.05% (w/v).

Examples of preservatives include methylparaben, ethylparaben, propylparaben, butylparaben, benzoic acid, sorbic acid, sodium benzoate, benzyl alcohol, phenylethanol, and the like. A blending amount of a preservative is, for example, 0.01% (w/v)-0.5% (w/v). However, in a suspension according to an embodiment of the present invention, surprisingly, growth of bacteria has not been observed even without a preservative, and thus, a preservative is not required.

A liquid medium (dispersion medium) used for a suspension for oral administration according to an embodiment of the present invention is preferably water, and may contain a pharmaceutically acceptable organic solvent. Examples of such an organic solvent include propylene glycol (1,2-propanediol), polyethylene glycol 300, polyethylene glycol 400, ethanol, and the like.

Embodiments of preferred composition combinations in the suspension of the present invention are illustrated below, but are not limited thereto.

(1) Edaravone particles, polyvinyl alcohol (dispersant), xanthan gum (thickening agent), sorbitol (sweetener), sodium bisulfite (stabilizer), L-cysteine hydrochloride (stabilizer), phosphoric acid (pH regulator), sodium hydroxide (pH regulator), simethicone emulsion (antifoaming agent), and water.

(2) Edaravone particles, polyvinyl alcohol (dispersant), tragacanth powder (thickening agent), sorbitol (sweetener), sodium bisulfite (stabilizer), L-cysteine hydrochloride (stabilizer), phosphoric acid (pH regulator), sodium hydroxide (pH regulator), simethicone emulsion (antifoaming agent), and water.

(3) Edaravone particles, sucrose fatty acid ester (dispersant), xanthan gum (thickening agent), sucrose (sweetener), sodium bisulfite (stabilizer), L-cysteine hydrochloride (stabilizer), acetic acid (pH regulator), sodium hydroxide (pH regulator), simethicone emulsion (antifoaming agent), and water.

(4) Edaravone particles, polyvinyl alcohol (dispersant), xanthan gum (thickening agent), sorbitol (sweetener), sodium bisulfite (stabilizer), phosphoric acid (pH regulator), sodium hydroxide (pH regulator), simethicone emulsion (antifoaming agent), and water.

(5) Edaravone particles, polyvinyl alcohol (dispersant), xanthan gum (thickening agent), sorbitol (sweetener), sodium bisulfite (stabilizer), L-cysteine hydrochloride (stabilizer), phosphoric acid (pH regulator), sodium hydroxide (pH regulator), simethicone emulsion (antifoam), fragrance, and water.

In a suspension according to an embodiment of the present invention, the edaravone particles maintain a well dispersed state for a long period of time. Therefore, even when a certain amount is dispensed from the whole solution, uniformity of drug content can be ensured. Further, a suspension according to an embodiment of the present invention has features such as the following: even when the edaravone particles have settled after a long period of time of storage, the edaravone particles can be redispersed quickly by shaking; chemical stability of edaravone is not impaired during such a long period of time of storage; and there is no growth of bacteria even without a preservative.

Further, in a drug product according to an embodiment of the present invention, by further blending a thickening agent, an effect is also achieved that the drug product is imparted with a moderate viscosity and thus can be easily taken even by a patient with dysphagia and a risk of aspiration is reduced, and, when the drug product is administered to humans, variation in drug concentration in blood among the patients is reduced, and a stable drug effect can be expected.

The suspension of the present invention exhibits excellent bioavailability. Therefore, a drug concentration transition in blood equivalent to that in a case where an edaravone injection currently used as an ALS therapeutic agent in a clinical setting, for example, "Radicut"' (registered trademark) of a Japanese brand name, was administered (60 mg as edaravone was intravenously injected over 1 hour) can be reached at a very low edaravone dose as an oral dose, specifically, 90-120 mg, more specifically 100-110 mg, and most specifically 105 mg.

Specifically, with respect to a suspension according to an embodiment of the present invention, when a crossover study is performed in a human using an edaravone injection as a control, a lower limit of a 90% confidence interval of a ratio of a Cmax geometric mean value with respect to the control drug product and a lower limit of a 90% confidence interval of a ratio of an $AUC_{0-\infty}$ geometric mean value with respect to the control drug product both exceed 0.8. In the above, an oral dose of a suspension according to an embodiment of the present is as edaravone is 90-120 mg, preferably 100-110 mg, and most preferably 105 mg, and an edaravone injection as the control drug product containing 60 mg of edaravone is injected intravenously over 1 hour. Further, in the above study, of a suspension according to an embodiment of the present invention, the lower limit of the 90% confidence interval of the ratio of the Cmax geometric mean value with respect to the control drug product exceeds 0.8, and the 90% confidence interval of the ratio of the $AUC_{0-\infty}$ geometric mean value with respect to the control drug product can be in a range of 0.8-1.25.

Further, in the above study, of a suspension according to an embodiment of the present invention, the 90% confidence interval of the ratio of the Cmax geometric mean value with respect to the control drug product is in a range of 0.8-2.0, and the 90% confidence interval of the ratio of the $AUC_{0-\infty}$ geometric mean value with respect to the control drug product can be in a range of 0.8-1.25.

Further, in the above, of a suspension according to an embodiment of the present invention, the 90% confidence interval of the ratio of the Cmax geometric mean value with respect to the control drug product is in a range of 0.8-1.5, and the 90% confidence interval of the ratio of the $AUC_{0-\infty}$ geometric mean value with respect to the control drug product can be in a range of 0.8-1.25.

Further, in the above, of a suspension according to an embodiment of the present invention, both the ratio of the Cmax geometric mean value with respect to the control drug product and the ratio of the $AUC_{0-\infty}$ geometric mean value with respect to the control drug product can be in a range of 0.8-1.25.

When a suspension according to an embodiment of the present invention (for example, 90-120 mg, more specifically 100-110 mg, and even more specifically 105 mg as edaravone) is orally administered to humans, a mean Cmax is in a range of 500-2500 ng/mL, and a mean $AUC_{0-\infty}$ is in a range of 1000-2500 h*ng/mL. In the above, more specifically, the mean Cmax is in a range of 1000-2000 ng/mL, and the mean $AUC_{0-\infty}$ is in a range of 1500-2000 h*ng/mL. The mean Cmax and the mean $AUC_{0-\infty}$ may each be an arithmetic mean value or a geometric mean value.

Examples of a suspension equivalent to the above edaravone injection include, but are not limited to, a suspension having the following composition.

Edaravone particles: 2.1% (w/v)
Polyvinyl alcohol (dispersant): 0.1% (w/v)
Xanthan gum (thickening agent): 0.3% (w/v)
Sorbitol (sweetener): 40% (w/v)
Sodium sulfite (stabilizer): 0.1% (w/v)
L-cysteine hydrochloride (stabilizer): 0.05% (w/v)
Sodium hydroxide (pH regulator): an appropriate amount
Phosphoric acid (pH regulator): an appropriate amount
Simethicone emulsion (antifoaming agent): 0.05% (w/v)
Dispersion medium: water By orally administering 5 mL of the suspension (105 mg as edaravone), concentration transition in a plasma equivalent to that in a case where an edaravone injection (60 mg as edaravone) is intravenously injected over 60 minutes is obtained.

A suspension for oral administration according to an embodiment of the present invention can be prepared by mixing the above-described edaravone particles, dispersant and other ingredients (thickening agent, sweetener, and the like) when necessary, and water.

The edaravone particles to be used preferably have a D50 particle size (volume-based cumulative 50% particle size) of 2 μm-50 μm and a D90 particle size (volume-based cumulative 90% particle size) of 100 μm-250 μm. In order to prepare edaravone particles having the above-described particle sizes, for example, when the edaravone particles are formed of only edaravone, an edaravone raw powder obtained using a method described in Japanese Patent Publication No. H5-31523 or the like can be adjusted into edaravone particles having the desired particle sizes using a pulverizer such as a jet mill, a hammer mill, a pin mill, or a ball mill. The particle sizes of the edaravone particles can be measured using a dry method using a laser diffraction particle size distribution device (Sympatec/HELOS & CUVETTE).

By changing the particle sizes of the edaravone particles to be used, it is possible to change a dissolution rate of edaravone from an obtained drug product. Specifically, the smaller the particle sizes, the faster the dissolution. For example, when the edaravone particles are a pulverized product of the edaravone raw powder obtained using the above method, a D50 particle size is in a range of 10 μm-50 μm, a D90 particle size is in a range of 50 μm-200 μm, and preferably the D50 particle size is in a range of 20 μm-40 μm and the D90 particle size in a range of 70 μm-150 μm. Thereby, when a dissolution test (test solutions: First Solution, Second Solution, 0.05 mol/L of acetic acid and sodium acetate buffer solution (pH 4.0), and the like; paddle rotation speed: 50 rpm-75 rpm) is performed according to Japanese Pharmacopoeia, a drug product having an edaravone dissolution rate of 80% or more 30 minutes after starting the test is obtained, and thus, a prompt drug effect can be expected.

For a suspension according to an embodiment of the present invention, after the components are blended, a homogeneous suspension can be prepared using a mixing method such as stirring, shaking, and ultrasonic irradiation.

An example of a suitable preparation method is a method in which edaravone particles are uniformly dispersed (suspended) in water in which a dispersant is dissolved (a dispersant solution). This case includes both putting the edaravone particles into the dispersant solution, and adding the dispersant solution to the edaravone particles.

Other components such as a thickening agent and a sweetener may be added to the dispersant solution in advance before dispersing the edaravone particles, or may be added at the same time as when the eradavone particles are dispersed, or may be added after the edaravone particles are dispersed. Further, the addition timing of these components may be different for each of the components.

The suspension for oral administration of the present invention is provided in a state in which the edaravone particles are suspended, which is preferable since there are few operations at the time of administration. However, a kit for preparation at the time of use may also be provided in which the edaravone particles and water are separated. An example of such a form is a kit for preparing an edaravone suspension that includes: (A) a solid composition containing the edaravone particles; and (B) a dispersant solution. The kit for preparation at the time of use can be expected to have storage stability over a longer period of time as compared to a prepared suspension.

(A) The solid composition containing edaravone particles may contain only edaravone particles, or may be a mixture containing also other components. As the edaravone particles, those used for preparing the suspension can be used. Further, the solid composition containing edaravone particles is granulated using a known method, and may be finely granulated or granulated, or compressed and tableted.

Also in (B) the dispersant solution, not only the dispersant to be used in the present invention, but other components such as a thickening agent and a sweetener may be added. A health care worker can mix (A) and (B) and shake the mixture to obtain a suspension according to an embodiment of the present invention.

Further, a suspension for oral administration according to an embodiment of the present invention may be provided in a form of a solid composition that allows a suspension according to an embodiment of the present invention to be prepared at the time of use by only adding water, that is, in a form of a solid composition that contains the edaravone particles and the dispersant. Of course, this solid composition may contain other ingredients used in a suspension according to an embodiment of the present invention such as a thickening agent and a sweetener. Further, this solid composition is granulated using a known method, and may be finely granulated, or granulated, or compressed and tableted.

In this embodiment, a health care worker can mix the solid composition containing the edaravone particles and the dispersant with water and shake the mixture to obtain a suspension according to an embodiment of the present invention.

A suspension according to an embodiment of the present invention is administered using an intermittent administration method, which is described in WO 2005/75434 and is currently used for ALS treatment using an edaravone injection in a clinical setting, that is, an administration method in which an administration period and a drug holiday period are taken as one unit and this is repeated twice or more. When an administration period and a drug holiday period are repeated two or more times, an end of this period is always a drug holiday period. However, it is not necessary to provide the last drug holiday period. That is, for example, when an administration period and a drug holiday period are repeated two times, this is a case of "an administration period, a drug holiday period, an administration period, and a drug holiday period; however, without providing the last drug holiday period, a case of "an administration period, a drug holiday period, and an administration period" is also possible.

A drug holiday period is a period in which drug administration is not performed continuously for 7 days or more, preferably 14 days.

An administration period can be 14 days, or 10 days out of 14 days. 10 days out of 14 days mean any 10 days out of 14 consecutive days. The 10 days in which drug administration is performed may be 10 consecutive days or 10 non-consecutive days separated by one or more periods in each of which drug administration is not performed for 1-4 days. As an administration period, a preferred period can be selected while observing a condition of a patient.

More specifically, an example is a method in which an initial drug holiday period of 14 days is provided after an initial administration period of 14 days, and then an administration period of 10 days out of 14 days and a drug holiday period of 14 days are repeated. The number of repetitions of the administration period of 10 days out of 14 days and the drug holiday period of 14 days is not particularly limited as long as the number of repetitions is 1 or more.

A daily dose in an intermittent administration period can be selected as appropriate according to an age and a condition (for example, severity of the disease) of a patient. In general, for an adult, a dose of edaravone is 60 mg-400 mg, preferably 60 mg-300 mg, more preferably 90 mg-210 mg, especially preferably 90 mg, 100 mg, 105 mg, 180 mg, 200 mg or 210 mg, even more preferably 105 mg or 210 mg, and most preferably 105 mg.

Or, a suspension according to an embodiment of the present invention may be administered to a patient daily or nearly daily during an administration period. A daily dose can be selected as appropriate according to an age and a condition (for example, severity of the disease) of a patient. In general, for an adult, a dose of edaravone is 60 mg-400 mg, preferably 60 mg-300 mg, more preferably 90 mg-210 mg, especially preferably 90 mg, 100 mg, 105 mg, 180 mg, 200 mg or 210 mg, even more preferably 105 mg or 210 mg, and most preferably 105 mg. In both daily administration and intermittent administration, the number of administrations per day is not limited, and a preferred number of administrations per day can be selected while observing a condition of the patient. However, in consideration of patient's burden and the like, the number of administrations per day is preferably 3, 2 or 1, and is more preferably 1.

Further, in the case of a suspension according to an embodiment of the present invention, edaravone can be contained at a high content. Therefore, a dose of a drug product containing edaravone of the above dose can be reduced, and this is advantageous for patients with dysphagia. For example, in the case of a suspension according to an embodiment of the present invention, an ALS therapeutic agent can be prepared for which a dose of a drug product per one oral administration is 1-20 mL and the dose contains 50-210 mg of edaravone.

Further, in addition to ALS, a suspension according to an embodiment of the present invention can also be used for diseases that have been reported to involve oxidative stress, for example, neurodegenerative diseases with motor dysfunction such as Parkinson's disease and spinocerebellar degeneration; muscle diseases such as muscular dystrophy; intracranial neurodegenerative diseases with cognitive impairment such as Alzheimer's disease; vascular disorders such as cerebral infarction; systemic inflammatory diseases such as multiple sclerosis and systemic scleroderma; and local inflammatory diseases such as stomatitis.

EXAMPLES

Next, the present invention is described in detail using examples and test examples. However, the present invention is not limited thereto.

Example 1

200 mg of polyvinyl alcohol (Nippon Synthetic Chemical Industry Co., Ltd., EG-05P) was dissolved in 200 mL of water to prepare a 0.1% (w/v) polyvinyl alcohol aqueous solution. 100 mg of edaravone particles (edaravone powder, D50: 37 μm; D90: 143 μm) was dispersed in 10 mL of the polyvinyl alcohol aqueous solution to obtain an edaravone suspension for oral administration.

Example 2

200 mg of polyvinyl alcohol (Nippon Synthetic Chemistry Industry Co., Ltd., EG-05P) was dissolved in 200 mL of water, and, in the resulting polyvinyl alcohol aqueous solution, 1000 mg of xanthan gum (Sansho Co., Ltd., KELTROL-CG) was further dissolved to prepare a 0.1% (w/v) polyvinyl alcohol/0.5% (w/v) xanthan gum aqueous solution. 100 mg of edaravone particles (edaravone powder, D50: 37 μm; D90: 143 μm) was dispersed in 10 mL of the polyvinyl alcohol/xanthan gum aqueous solution to obtain an edaravone suspension.

Example 3

200 mg of polyvinyl alcohol (Nippon Synthetic Chemistry Industry Co., Ltd., EG-05P) was dissolved in 200 mL of water, and, in the resulting polyvinyl alcohol aqueous solution, 1000 mg of tragacanth powder (Suzu Funmatsu Yakuhin K.K.) was further dissolved to prepare a 0.1% (w/v) polyvinyl alcohol/0.5% (w/v) tragacanth powder aqueous solution. 100 mg of edaravone particles (edaravone powder, D50: 37 μm; D90: 143 μm) was dispersed in 10 mL of the polyvinyl alcohol/tragacanth powder aqueous solution to obtain an edaravone suspension.

Example 4

200 mg of methylcellulose (Shin-Etsu Chemical Co., Ltd., SM-25) was dissolved in 200 mL of water to prepare a 0.1% (w/v) methylcellulose aqueous solution. 100 mg of edaravone particles (edaravone powder, D50: 37 μm; D90: 143 μm) was dispersed in 10 mL of the methylcellulose aqueous solution to obtain an edaravone suspension.

Example 5

200 mg of methylcellulose (Shin-Etsu Chemical Co., Ltd., SM-25) was dissolved in 200 mL of water, and, in the resulting methylcellulose aqueous solution, 1000 mg of xanthan gum (Sansho Co., Ltd., KELTROL-CG) was further dissolved to prepare a 0.1% (w/v) methylcellulose/0.5% (w/v) xanthan gum aqueous solution. 100 mg of edaravone particles (edaravone powder, D50: 37 μm; D90: 143 μm) was dispersed in 10 mL of the methylcellulose/xanthan gum aqueous solution to obtain an edaravone suspension.

Example 6

200 mg of methylcellulose (Shin-Etsu Chemical Co., Ltd., SM-25) was dissolved in 200 mL of water, and, in the resulting methylcellulose aqueous solution, 1000 mg of tragacanth powder (Suzu Funmatsu Yakuhin K.K.) was further dissolved to prepare a 0.1% (w/v) methylcellulose/0.5% (w/v) tragacanth powder aqueous solution. 100 mg of edaravone particles (edaravone powder, D50: 37 μm; D90: 143 μm) was dispersed in 10 mL of the methylcellulose/tragacanth powder aqueous solution to obtain an edaravone suspension.

Example 7

200 mg of polyvinyl alcohol (Nippon Synthetic Chemistry Industry Co., Ltd., EG-05P) was dissolved in 200 mL of water, and, in the resulting polyvinyl alcohol aqueous solution, 1600 mg of carmellose sodium (Daicel FineChem Ltd., CMC Daicel 1150) was further dissolved to prepare a 0.1% (w/v) polyvinyl alcohol/0.5% (w/v) carmellose sodium aqueous solution. 100 mg of edaravone particles (edaravone powder, D50: 37 μm; D90: 143 μm) was dispersed in 10 mL of the polyvinyl alcohol/carmellose sodium aqueous solution to obtain an edaravone suspension.

Example 8

200 mg of polyvinyl alcohol (Nippon Synthetic Chemistry Industry Co., Ltd., EG-05P) was dissolved in 200 mL of water, and, in the resulting polyvinyl alcohol aqueous solution, 160 g of Dextrin (Nippon Starch Chemical Co., Ltd., Akadama 3) was further dissolved to prepare a 0.1% (w/v) polyvinyl alcohol/0.5% (w/v) dextrin aqueous solution. 100 mg of edaravone particles (edaravone powder, D50: 37 μm; D90: 143 μm) was dispersed in 10 mL of the polyvinyl alcohol/dextrin aqueous solution to obtain an edaravone suspension.

Example 9

200 mg of methylcellulose (Shin-Etsu Chemical Co., Ltd., SM-25) was dissolved in 200 mL of water, and, in the resulting methylcellulose aqueous solution, 1600 mg of carmellose sodium (Daicel FineChem Ltd., CMC Daicel 1150) was further dissolved to prepare a 0.1% (w/v) methylcellulose/0.5% (w/v) carmellose sodium aqueous solution. 100 mg of edaravone particles (edaravone powder, D50: 37 μm; D90: 143 μm) was dispersed in 10 mL of the methylcellulose/carmellose sodium aqueous solution to obtain an edaravone suspension.

Example 10

200 mg of methylcellulose (Shin-Etsu Chemical Co., Ltd., SM-25) was dissolved in 200 mL of water, and, in the resulting methylcellulose aqueous solution, 160 g of Dextrin (Nippon Starch Chemical Co., Ltd., Akadama 3) was further dissolved to prepare a 0.1% (w/v) methylcellulose/0.5% (w/v) dextrin aqueous solution. 100 mg of edaravone particles (edaravone powder, D50: 37 μm; D90: 143 μm) was dispersed in 10 mL of the methylcellulose/dextrin aqueous solution to obtain an edaravone suspension.

Example 11

40 mg of polyvinyl alcohol (Nippon Synthetic Chemical Industry Co., Ltd., EG-05P), 20 mg of simethicone emulsion (Basildon, PD30S) and 800 mg of edaravone particles (edaravone powder, D50: 37 μm, D90: 143 μm) were dissolved or dispersed in water such that a volume of the mixture became 40 mL, and an edaravone suspension for oral administration was obtained.

Example 12

40 mg of polyvinyl alcohol (Nippon Synthetic Chemical Industry Co., Ltd., EG-05P), 20 mg of simethicone emulsion (Basildon, PD30S), 80 mg of xanthan gum (Sansho Co., Ltd., KELTROL-CG), and 800 mg of edaravone particles (edaravone powder, D50: 37 μm, D90: 143 μm) were dissolved or dispersed in water such that a volume of the mixture became 40 mL, and an edaravone suspension for oral administration was obtained.

Example 13

40 mg of polyvinyl alcohol (Nippon Synthetic Chemical Industry Co., Ltd., EG-05P), 20 mg of simethicone emulsion (Basildon, PD30S), 120 mg of xanthan gum (Sansho Co., Ltd., KELTROL-CG), and 800 mg of edaravone particles (edaravone powder, D50: 37 μm, D90: 143 μm) were dissolved or dispersed in water such that a volume of the mixture became 40 mL, and an edaravone suspension for oral administration was obtained.

Example 14

40 mg of polyvinyl alcohol (Nippon Synthetic Chemical Industry Co., Ltd., EG-05P), 20 mg of simethicone emulsion (Basildon, PD30S), 200 mg of xanthan gum (Sansho Co., Ltd., KELTROL-CG), and 800 mg of edaravone particles (edaravone powder, D50: 37 μm, D90: 143 μm) were dissolved or dispersed in water such that a volume of the mixture became 40 mL, and an edaravone suspension for oral administration was obtained.

Example 15

40 mg of polyvinyl alcohol (Nippon Synthetic Chemical Industry Co., Ltd., EG-05P), 20 mg of simethicone emulsion (Basildon, PD30S), 4 g of D-sorbitol, 40 mg of xanthan gum (Sansho Co., Ltd., KELTROL-CG), and 800 mg of edaravone particles (edaravone powder, D50: 37 μm, D90: 143 μm) were dissolved or dispersed in water such that a volume of the mixture became 40 mL, and an edaravone suspension for oral administration was obtained.

Example 16

40 mg of polyvinyl alcohol (Nippon Synthetic Chemical Industry Co., Ltd., EG-05P), 20 mg of simethicone emulsion (Basildon, PD30S), 4 g of D-sorbitol, 120 mg of xanthan gum (Sansho Co., Ltd., KELTROL-CG), and 800 mg of edaravone particles (edaravone powder, D50: 37 μm, D90: 143 μm) were dissolved or dispersed in water such that a volume of the mixture became 40 mL, and an edaravone suspension for oral administration was obtained.

Example 17

40 mg of polyvinyl alcohol (Nippon Synthetic Chemical Industry Co., Ltd., EG-05P), 20 mg of simethicone emulsion (Basildon, PD30S), 4 g of D-sorbitol, 200 mg of xanthan gum (Sansho Co., Ltd., KELTROL-CG), and 800 mg of edaravone particles (edaravone powder, D50: 37 μm, D90: 143 μm) were dissolved or dispersed in water such that a volume of the mixture became 40 mL, and an edaravone suspension for oral administration was obtained.

Example 18

40 mg of polyvinyl alcohol (Nippon Synthetic Chemical Industry Co., Ltd., EG-05P), 40 mg of sodium bisulfite, 20 mg of L-cysteine hydrochloride hydrate, 20 mg of simethicone emulsion (Basildon, PD30S), 4 g of D-sorbitol, 120 mg of xanthan gum (Sansho Co., Ltd., KELTROL-CG), and 800 mg of edaravone particles (edaravone powder, D50: 37 μm, D90: 143 μm) were dissolved or dispersed in water such that a volume of the mixture became 40 mL, and into the resulting suspension, sodium hydroxide and phosphoric acid were added in appropriate amounts to adjust a pH thereof to 4.20, and an edaravone suspension was obtained.

Example 19

40 mg of benzoic acid, 2 mg of propylparaben, and 2 mg of butylparaben were dissolved in 40 mg of ethanol to prepare a preservative solution. 40 mg of polyvinyl alcohol (Nippon Synthetic Chemical Industry Co., Ltd., EG-05P), 40 mg of sodium bisulfite, 20 mg of L-cysteine hydrochloride hydrate, 20 mg of simethicone emulsion (Basildon, PD30S), 4 g of D-sorbitol, 120 mg of xanthan gum (Sansho Co., Ltd., KELTROL-CG), and 800 mg of edaravone particles (edaravone powder, D50: 37 μm, D90: 143 μm) were dissolved or dispersed in water such that a volume of the mixture became 40 mL, and after that, the preservative solution was added. Into the resulting suspension, sodium hydroxide and phosphoric acid were added in appropriate amounts to adjust a pH thereof to 4.20, and an edaravone suspension was obtained.

Example 20

200 mg of polyvinyl alcohol (Nippon Synthetic Chemical Industry Co., Ltd., EG-05P) was dissolved in 200 mL of purified water to prepare a 0.1% (w/v) polyvinyl alcohol solution. 120 mg of edaravone particles (edaravone powder, D50: 37 μm, D90: 143 μm) was dispersed in 10 mL of the polyvinyl alcohol solution to obtain an edaravone suspension.

Example 21

300 mg of edaravone particles (edaravone powder, D50: 37 μm, D90: 143 μm) was dispersed in 10 mL of the 0.1% (w/v) polyvinyl alcohol solution obtained in Example 20 to obtain an edaravone suspension.

Example 22

200 mg of polyvinyl alcohol (Nippon Synthetic Chemical Industry Co., Ltd., EG-05P) and 1000 mg of xanthan gum (Sansho Co., Ltd., KELTROL-CG) were dissolved in 200 mL of purified water to prepare a 0.1% (w/v) polyvinyl alcohol/0.5% (w/v) xanthan gum solution. 300 mg of edaravone particles (edaravone powder, D50: 37 μm, D90: 143 μm) was dispersed in 10 mL of the polyvinyl alcohol/xanthan gum solution to obtain an edaravone suspension.

Example 23

An edaravone suspension was obtained by using edaravone particles (edaravone powder, D50: 19 μm, D90: 73 μm) instead of the edaravone particles (edaravone powder, D50: 37 μm, D90: 143 μm) in Example 19.

Example 24

An edaravone suspension was obtained by using edaravone particles (edaravone powder, D50: 32 μm, D90: 110 μm) instead of the edaravone particles (edaravone powder, D50: 37 μm, D90: 143 μm) in Example 19.

Example 25

An edaravone suspension was obtained by using edaravone particles (edaravone powder, D50: 44 μm, D90: 204 μm) instead of the edaravone particles (edaravone powder, D50: 37 μm, D90: 143 μm) in Example 19.

Example 26

40 mg of polyvinyl alcohol (Nippon Synthetic Chemical Industry Co., Ltd., EG-05P), 40 mg of sodium bisulfate, 20 mg of L-cysteine hydrochloride hydrate, 20 mg of simethicone emulsion (Basildon, PD30S), 16 g of D-sorbitol, 120 mg of xanthan gum (Sansho Co., Ltd., KELTROL-CG), and 840 mg of edaravone particles (edaravone powder, D50: 37 μm, D90: 143 μm) were dissolved or dispersed in water such that a volume of the mixture became 40 mL, and into the resulting suspension, sodium hydroxide and phosphoric acid were added in appropriate amounts to adjust a pH thereof to 4.20, and an edaravone suspension was obtained.

Example 27

An edaravone suspension was obtained by using edaravone particles (edaravone powder, D50: 17 μm, D90: 64 μm) instead of the edaravone particles (edaravone powder, D50: 37 μm, D90: 143 μm) in Example 26.

Example 28

An edaravone suspension was obtained by using edaravone particles (edaravone powder, D50: 21 μm, D90: 79 μm) instead of the edaravone particles (edaravone powder, D50: 37 μm, D90: 143 μm) in Example 26.

Example 29

An edaravone suspension was obtained by using edaravone particles (edaravone powder, D50: 31 μm, D90: 124 μm) instead of the edaravone particles (edaravone powder, D50: 37 μm, D90: 143 μm) in Example 26.

Example 30

An edaravone suspension was obtained by using edaravone particles (edaravone powder, D50: 46 μm, D90: 185

μm) instead of the edaravone particles (edaravone powder, D50: 37 μm, D90: 143 μm) in Example 26.

Example 31

An edaravone suspension was obtained by using 200 mg of tragacanth powder (Suzu Funmatsu Yakuhin K.K.) instead of 120 mg of xanthan gum (Sansho Co., Ltd., KELTROL-CG) in Example 26.

Test Example 1 (Selection of Dispersant)

0.1% (w/v) aqueous solutions of drug product additives described in the following table that are substances having a function capable of dispersing solid particles in a liquid were prepared at a room temperature.

50 mL of each of the aqueous solutions of the additives was added to 3600 mg of edaravone particles (edaravone powder, D50: 37 μm, D90: 143 μm) and the mixture was stirred using a stirrer. The results are shown in the following table.

powder, D50: 37 μm, D90: 143 μm) and the mixture was stirred using a stirrer for 30 minutes or more, and a dispersed state of the edaravone particles was confirmed.

Further, 20 mL of the dispersion liquid obtained above was filled into a sample bottle (inner diameter: 25 mm×outer diameter: 27.5 mm×height: 72 mm), and measurement of a transmission scattering light intensity ΔT % at a height of 39-40 mm of the sample bottle was started using a TURBISCAN Tower (manufactured by Formulaction) (with a temperature set to 25° C.), and a value obtained after 10 minutes after the start of the measurement was defined as the transmission scattering light intensity ΔT % for each additive. The transmission scattering light intensities ΔT % of the additives and the dispersion state of the edaravone particles in the additive solutions are shown in the following table.

TABLE 1

| | Appearance observation results on dispersibility | |
|---|---|---|
| Additive Name | No secondary aggregation | No floating on liquid surface |
| Gum Arabic Powder (Kozakai Pharmaceutical Co., Ltd.) | Δ | X |
| Bentonite (HOJUN Co., Ltd., Wenger FW) | Δ | X |
| Polyvinyl Alcohol (Nippon Synthetic Chemical Industry Co., Ltd., EG-03P) | ○ | ○ |
| Sodium Alginate (KIMICA Corporation, ULV-L3) | X | X |
| Xanthan Gum (Sansho Co., Ltd., KELTROL-CG) | X | |
| Sucrose Fatty Acid Ester (Mitsubishi-Chemical Foods Corporation, S-1170F) | ○ | ○ |
| Tragacanth Powder (Suzu Funmatsu Yakuhin K.K.) | Δ | X |
| Methylcellulose (Shin-Etsu Chemical Co., Ltd., SM-25) | ○ | ○ |
| Hypromellose (Shin-Etsu Chemical Co., Ltd., TC-5E) | ○ | ○ |
| Carmellose Sodium (Daicel FineChem Ltd., CMC Daicel 1150) | X | X |

○: There is no secondary aggregation ○: There is no floating
Δ: There is some secondary aggregation Δ: There is some floating
X: There is secondary aggregation X: There is floating From the results of the above table, it is found that only polyvinyl alcohol, methylcellulose, sucrose fatty acid ester, and hypromellose can suitably disperse edaravone particles in water.

Test Example 2 (Transmission Scattering Light Intensity Test)

0.1% (w/v) aqueous solutions of drug product additives described in the following table that are substances having a function capable of dispersing solid particles in a liquid were prepared at a room temperature.

40 mL of each of the aqueous solutions of the additives was added to 840 mg of edaravone particles (edaravone

TABLE 2

| Additive Name | Transmission Scattering light Intensity ΔT % | Dispersion State of Edaravone |
|---|---|---|
| Polyvinyl Alcohol (Nippon Synthetic Chemical Industry Co., Ltd., EG-03P) | 32.100 | dispersed |
| Methylcellulose (Shin-Etsu Chemical Co., Ltd., SM-15) | 3.038 | dispersed |
| Sucrose Fatty Acid Ester (Mitsubishi-Chemical Foods Corporation, S-1170F)) | 8.767 | dispersed |
| Hypromellose (Shin-Etsu Chemical Co., Ltd., TC-5E) | 17.542 | dispersed |

TABLE 2-continued

| Additive Name | Transmission Scattering light Intensity ΔT % | Dispersion State of Edaravone |
|---|---|---|
| Gum Arabic Powder (Kozakai Pharmaceutical Co., Ltd.) | 0.070 | not dispersed |
| Bentonite (HOJUN Co., Ltd., Wenger FW) | 0.012 | not dispersed |
| Tragacanth Powder (Suzu Funmatsu Yakuhin K.K.) | 0.000 | not dispersed |
| Sodium Alginate (KIMICA Corporation, ULV-L3) | 0.012 | not dispersed |
| Xanthan Gum (Sansho Co., Ltd., KELTROL-CG) | 0.007 | not dispersed |
| Carmellose Sodium (Daicel FineChem Ltd., CMC Daicel 1150) | 0.001 | not dispersed |
| Polyvinyl Alcohol (Nippon Synthetic Chemical Industry Co., Ltd., EG-05P) | 15.543 | dispersed |
| MACROGOL 6000 | 0.000 | not dispersed |
| D-sorbitol | 0.000 | not dispersed |
| Polysorbate 80 | 6.151 | dispersed |

From the results of the above table, it can be seen that a dispersant that can suitably disperse edaravone particles has a transmission scattering light intensity ΔT % of 1% or more.

Test Example 3 (Contact Angle Test)

120 mg of an edaravone drug substance (D50: 37 μm, D90: 143 μm) was compression-molded using a single-punch tableting machine (Compaction Analyzer) (punch: flat punch having a diameter of 8 mm; tableting pressure: 800 kgf), and an edaravone tablet for contact angle measurement was obtained.

Edaravone saturated aqueous solutions in which drug product additives described in the following table that are substances having a function capable of dispersing solid particles in a liquid were dissolved 0.1% (w/v) therein were prepared at a room temperature, and contact angles with respect to the edaravone tablet prepared above were measured using a contact angle measurement device (Kyowa Interface Science, Inc., CAX-150). The results are shown in the following table.

Syringe used: glass, 1 mL
Needle: 23 gauge
Liquid volume: 1 μL
Measurement Time: after 3.1 seconds

TABLE 3

| Additive Name | Contact Angle |
|---|---|
| Polyvinyl Alcohol (Nippon Synthetic Chemical Industry Co., Ltd., EG-03P) | 69.8 |
| Sucrose Fatty Acid Ester (Mitsubishi-Chemical Foods Corporation, S-1170F) | 74.3 |
| Hypromellose (Shin-Etsu Chemical Co., Ltd., TC-5E)) | 78.8 |
| Gum Arabic Powder (Kozakai Pharmaceutical Co., Ltd.) | 89.5 |
| Bentonite (HOJUN Co., Ltd., Wenger FW) | 86.9 |
| Tragacanth Powder (Suzu Funmatsu Yakuhin K.K.) | 83.9 |
| Sodium Alginate (KIMICA Corporation, ULV-L3) | 86.4 |
| Xanthan Gum (Sansho Co., Ltd., KELTROL-CG) | 84.0 |
| Carmellose Sodium (Daicel FineChem Ltd., CMC Daicel 1150) | 87.3 |
| Polyvinyl Alcohol (Nippon Synthetic Chemical Industry Co., Ltd., EG-05P) | 79.8 |
| D-sorbitol | 83.3 |
| Polysorbate 80 | 53.1 |

From the above results and the results of Test Example 1 or 2, it can be seen that a substance which exhibits a contact angle of 80 degrees or less for edaravone saturated aqueous solution containing 0.1% (w/v) additive with respect to the edaravone tablet can suitably disperse edaravone in water.

Test Example 4 (Stability)

5 mL of each of the edaravone suspensions prepared in Examples 1-10 was put in a glass bottle and was sealed, and was stored at 60° C. for 4 weeks. After 4 weeks, an amount of edaravone-related substances in each suspension was measured according to Related Substances (i) in Purity Test described in Edaravone Injection in Japanese Pharmacopeia. The results are shown in the following table.

TABLE 4

| Example | Related Substance Amount (%) |
|---|---|
| 1 | 0.90 |
| 2 | 1.60 |
| 3 | 1.03 |
| 4 | 1.00 |
| 5 | 1.47 |
| 6 | 0.95 |
| 7 | 4.60 |
| 8 | 4.41 |
| 9 | 4.75 |
| 10 | 3.87 |

From the above results, it can be seen that, although an amount of edaravone-related substances generated in any one of Examples 1-10 is small, the amounts of the edaravone-related substances generated in the suspensions of Examples 1-6 in which xanthan gum or tragacanth powder was used as a thickening agent are particularly small.

Test Example 5 (Content Uniformity Test)

From each of the edaravone suspensions (40 mL each) obtained in Examples 11-14, 5 mL of the suspension was sampled each time using a syringe, and the sampling was performed 7 times in total. The edaravone content in the 5 mL of the sampled suspension was measured. The results are shown below (values in the table are relative values (%) with respect to 100 mg of edaravone contained in 5 mL of the original suspension).

TABLE 5

| Number of sampling times | Example 11 | Example 12 | Example 13 | Example 14 |
|---|---|---|---|---|
| First time | 114.2 | 98.4 | 101.1 | 98.2 |
| Second time | 97.3 | 97.7 | 99.7 | 101.4 |
| Third time | 100.2 | 98.8 | 100.6 | 99.6 |
| Fourth time | 89.1 | 101.0 | 100.4 | 100.1 |
| Fifth time | 94.1 | 99.0 | 101.6 | 103.0 |
| Sixth time | 92.8 | 99.4 | 99.2 | 101.1 |
| Seventh time | 92.5 | 100.9 | 101.5 | 100.3 |
| Average | 97.2 | 99.3 | 100.6 | 100.7 |

Content uniformity is ensured in all the suspensions, and particularly, a more preferable content uniformity is exhibited in the suspensions of Examples 12-14 that each contain a thickening agent.

Test Example 6 (Redispersibility Test)

Each of the suspensions obtained in Examples 15-17 was put in a centrifugal separator and a gravity of 4000 g was applied thereto for 6.6 hours, and the edaravone particles were forced to settle. After completion of the centrifugation, each of the suspensions was shaken lightly by hand. The edaravone particles in each of the suspensions of Examples 15 and 16 were redispersed within 10 seconds, and the edaravone particles in the drug product of Example 17 were redispersed within 40 seconds. The above gravity condition is equivalent to 3 years of storage.

Test Example 7 (Preservation Efficacy Test)

Preservation efficacy tests were performed according to Japanese Pharmacopeia using the suspensions obtained in Examples 18-19. Although a preservative was not blended, the suspension of Example 18 exhibited a preservative effect equivalent to that of the suspension of Example 19 in which a preservative was blended.

TABLE 6

| | | Bacterial Count (CFU/mL) | | | |
|---|---|---|---|---|---|
| | | Example 18 | | Example 19 | |
| Bacterial Strain | Initial | 14 days later | 28 days later | 14 days later | 28 days later |
| Pseudomonas aeruginosa ATCC9027 | $0.35 \times 10^6$ | 0 | 0 | 0 | 0 |
| Escherichia coli ATCC8739 | $0.33 \times 10^6$ | 0 | 0 | 0 | 0 |
| Staphylococus aeruginosa ATCC6538 | $1.38 \times 10^6$ | 0 | 0 | 0 | 0 |
| Candida albicans ATCC10231 | $0.42 \times 10^6$ | 0 | 0 | 0 | 0 |
| Aspergillus brasiliensis ATC 16404 | $0.64 \times 10^6$ | 0 | 0 | 0 | 0 |

Test Example 8

The edaravone suspensions (10 mL) obtained in Examples 20-22 were each orally administered to 6 healthy adult males in a fasting state. Blood samples were collected before and 0.25, 0.5, 1, 1.5, 2, 4, 6, 8, 12, 24, 36, and 48 hours after administration, and unchanged edaravone concentration in plasma was measured. The obtained PK profiles are shown in the following table.

TABLE 7

| Administered drug product | Edaravone dose (mg) | $t_{max}$ (h) (SD) | $C_{max}$ (ng/mL) (SD) | $AUC_{0-24\,h}$ (h * ng/mL) (SD) | $t_{1/2}$ (h) (SD) |
|---|---|---|---|---|---|
| Example 20 (N = 6) | 120 | 0.38 (0.14) | 1735 (738.0) | 2241.77 (910.63) | 5.13 (1.46) |
| Example 21 (N = 6) | 300 | 0.75 (0.42) | 5426 (2496) | 9034.06 (2737.73) | 9.05 (3.31) |
| Example 22 (N = 6) | 300 | 0.55 (0.25) | 8805 (933.2) | 11318.84 (1053.43) | 11.76 (4.09) |

Cmax and $AUC_{0-24h}$ of Example 20 (edaravone: 120 mg) significantly exceeded Cmax (1049 ng/mL) and $AUC_{0-24h}$ (1374 h*ng/mL) of an edaravone injection (60 mg) described in Amyotroph Lateral Scler Frontotemporal Degener.2017; 18 (suppl 1): 80-87. It can be seen that a suspension according to an embodiment of the present invention has excellent bioavailability as a drug product for oral administration.

Further, from a comparison between the PK profiles of Examples 21 and 22, it can be seen that, by adding a thickening agent, variation in edaravone concentration in plasma among the subjects is reduced, that is, a stable drug effect can be expected.

Test Example 9 (1) (Dissolution Test)

The suspensions prepared in Examples 19, 23, 24, and 25 were subjected to dissolution tests according to Dissolution Test Method 2 (Paddle Method) of Japanese Pharmacopoeia.

Eluate: 900 ml of the first solution (pH 1.2) or the second solution (pH 6.8) of Dissolution Test of Japanese Pharmacopoeia Measurement method: absorbance at a wavelength of 240 nm Paddle rotation speed: 50 rpm Number of samples: n=3

Edaravone dissolution rates 30 minutes after starting tests and similarities of dissolution behaviors of other examples when the drug product of Example 19 was used as a standard drug product were determined according to Bioequivalence Guidelines for generic drugs, and calculation results of F2 functions with 15, 30, and 45 minutes as dissolution rate comparison times are shown in the following table. It is found that a smaller the particle size of the edaravone used to prepare the edaravone suspension leads to faster dissolution, and the dissolution rate can be controlled by changing the particle size of the edaravone particles. On the other hand, from the F2 function values, in First Solution (pH 1.2), the drug products of Examples 23-25 exhibited dissolution behaviors biologically equivalent to that of the drug product of Example 19, and, in Second Solution (pH 6.8), the drug products of Examples 23 and 24 exhibited dissolution behaviors biologically equivalent to that of the drug product of Example 19.

TABLE 8

| Edaravone suspension and particle sizes of edaravone powder used | First Solution (pH 1.2) | | Second Solution (pH 6.8) | |
|---|---|---|---|---|
| | Dissolution rate after 30 minutes | F2 function value (determination result*) | Dissolution rate after 30 minutes | F2 function value (determination result*) |
| Example 23 D50: 19 μm D90: 73 μm | 96% | 96.1 (equivalent to standard drug product) | 95% | 86.2 (equivalent to standard drug product) |
| Example 24 D50: 32 μm D90: 110 μm | 96% | 97.4 (equivalent to standard drug product) | 92% | 95.4 (equivalent to standard drug product) |
| Example 19 D50: 37 μm D90: 143 μm | 96% | Standard drug product | 93% | Standard drug product |
| Example 25 D50: 44 μm D90: 204 μm | 87% | 56.0 (equivalent to standard drug product) | 74% | 42.4 (not equivalent to standard drug product) |

*An F2 function value of 50 or more is equivalent to the standard drug product.

Test Example 9 (2) (Dissolution Test)

The suspensions prepared in Examples 27-30 were subjected to dissolution tests according to Dissolution Test Method 2 (Paddle Method) of Japanese Pharmacopoeia.
Eluate: 900 ml of 0.05 mol/L acetic acid/sodium acetate buffer solution (pH 4.0) 900 ml
Measurement method: absorbance at a wavelength of 240 nm
Paddle rotation speed: 50 rpm
Number of samples: n=3
Edaravone dissolution rates 30 minutes after starting tests and similarities of dissolution behaviors of other examples when the drug product of Example 29 was used as a standard drug product were determined according to Bioequivalence Guidelines for generic drugs, and calculation results of F2 functions with 15, 30, and 45 minutes as dissolution rate comparison times are shown in the following table. It is found that a smaller the particle size of the edaravone used to prepare the edaravone suspension leads to faster dissolution, and the dissolution rate can be controlled by changing the particle size of the edaravone particles. On the other hand, from the F2 function values, it can be seen that the drug products of Examples 27, 28 and 30 exhibit dissolution behaviors biologically equivalent to that of the drug product of Example 29.

TABLE 9

| Edaravone Suspension (values in parentheses are particle sizes of edaravone power used) | Dissolution rate after 30 minutes | F2 function value (determination result*) |
|---|---|---|
| Example 27 (D50: 19 μm, D90: 73 μm) | 100% | 96.1 (equivalent to standard drug product) |
| Example 28 (D50: 32 μm, D90: 110 μm) | 100% | 97.4 (equivalent to standard drug product) |
| Example 29 (D50: 37 μm, D90: 143 μm) | 98% | Standard drug product |
| Example 30 (D50: 44 μm, D90: 204 μm) | 94% | 56.0 (equivalent to standard drug product) |

*An F2 function value of 50 or more is equivalent to the standard drug product.

Test Example 10 (Bioequivalence Test)

The suspension obtained in Example 26 was subjected to an unblinded, single-dose, randomized crossover study in 42 Japanese healthy subjects using an edaravone injection as a target drug.

The administration of the edaravone suspension of Example 26 was performed by lightly shaking a glass bottle containing the suspension, extracting 5 mL (105 mg as edaravone) of the suspension with a syringe for oral administration, and orally administering the extracted suspension to a subject in a fasting state.

The administration of the edaravone injection was performed by intravenously injecting 200 mL of the edaravone injection (Radicut injection) (60 mg as edaravone) into a subject in a fasting state over 1 hour.

The PK profile of unchanged edaravone in plasma at the time of administration of suspension described in Example 26 and PK profile of unchanged edaravone in plasma at the time of administration of the edaravone injection are shown in FIGURE and the following table.

TABLE 10

| Administered drug product | Edaravone dose (mg) | $C_{max}$ (ng/mL) (SD) | $AUC_{0-\infty}$ (h * ng/mL) (SD) |
|---|---|---|---|
| Example 26 (po) | 105 (N = 42) | 1656 (734) | 1762 (540) |
| Edaravone Injection (iv) | 60 (N = 42) | 1253 (229) | 1736 (331) |

Further, bioequivalence evaluation results of the drug product of Example 26 with respect the edaravone injection are shown in the following table.

TABLE 11

| Parameter | Ratio (po/iv) of geometric mean value | 90% confidence interval of ratio of geometric mean value |
|---|---|---|
| $C_{max}$ (ng/mL) | 1.217 | 1.090-1.359 |
| $AUC_{0-\infty}$ (h * ng/mL) | 0.977 | 0.917-1.041 |

The ratio of the geometric mean value of Cmax or $AUC_{0-\infty}$ at the time of administration of the drug product of Example 26 with respect to the edaravone injection at the time of administration was within a range of 0.8-1.25 for both Cmax and $AUC_{0-\infty}$. The 90% confidence interval of the ratio of the geometric mean value was within the range of 0.8-1.25 for $AUC_{0-\infty}$. For Cmax, a lower limit of the 90% confidence interval of the ratio of the geometric mean value was within the range of 0.8-1.25, but an upper limit thereof exceeded the range.

An edaravone suspension according to an embodiment of the present invention is particularly useful as an ALS therapeutic agent. Therefore, the present invention has industrial applicability.

Currently, edaravone is used as an ALS therapeutic agent. However, edaravone as an ALS therapeutic agent is provided only as an injection, and an orally administered drug product is desired that is less burdensome for patients and caregivers and is preferable from a QOL perspective.

However, unlike an injection administered directly into blood, for a drug product for oral administration for which various factors such as absorption from the gastrointestinal tract and a first-pass effect affect bioavailability, obtaining a drug product biologically equivalent to an injection is difficult.

As drug products for oral administration, solid drug products such as tablets and capsules are common. However, for ALS patients who are expected to have declined swallowing ability, it is difficult to take the drug products of these forms directly. For these patients, oral administration forms such as liquids and suspensions are desirable.

Journal of Pharmaceutical Sciences 103:730-742, 2014, International Journal of Pharmaceutics 515 (2016) 490-500, and Drug Delivery, 24:1, 962-978 describe CMC-Na suspensions of edaravone. However, it is described that when these suspensions were administered to animals, all of them had low bioavailability.

Japanese Patent Application Laid-Open Publication No. 2004-91441 describes an edaravone solution for oral administration using an aqueous solution of tragacanth gum, and it is described that a sufficient concentration in blood was obtained in rats. However, the concentration in blood is lower than a result of the CMC-Na suspension described in Journal of Pharmaceutical Sciences 103:730-742, 2014, International Journal of Pharmaceutics 515 (2016) 490-500, and Drug Delivery, 24:1, 962-978, and a drug product described in the document does not have bioavailability comparable to that of an injection either.

To overcome low bioavailability in suspensions, International Publication No. WO 2018/134243 describes an edaravone solution having excellent absorbability. However, due to low solubility of edaravone in water, a dose of this solution becomes as high as 100 mL and thus is not preferable from a perspective of medication adherence of patients. The entire contents of these publications are incorporated herein by reference.

An edaravone suspension for oral administration according to an embodiment of the present invention can reduce burden on ALS patients and caregivers and achieve an ALS therapeutic effect equivalent to that of an injection.

As a result of studies, by blending a dispersant, edaravone particles can be uniformly dispersed in water and the dispersed state can be maintained, and, even when the edaravone particles have settled after storage, the edaravone particles can be quickly redispersed by light shaking, and thus, a pharmaceutically superior edaravone suspension for oral administration can be prepared. Further, based on the findings of Journal of Pharmaceutical Sciences 103:730-742, 2014, International Journal of Pharmaceutics 515 (2016) 490-500, and Drug Delivery, 24:1, 962-978, a prepared edaravone suspension for oral administration is a suspension considered to be disadvantageous from a perspective of bioavailability based on results of previous animal experiments. A suspension according to an embodiment of the present invention exhibits unexpectedly superior bioavailability when being administered to humans, and thus accomplished the present invention.

According to an embodiment of the present invention, an edaravone suspension for human oral administration contains: edaravone particles; a dispersant; and water.

In the suspension, the dispersant may be a dispersant exhibiting a transmission scattering light intensity of 1% or more.

In the suspension, the dispersant may be a dispersant exhibiting a contact angle of 80 degrees or less.

In the suspension, the dispersant may be one or two selected from polyvinyl alcohol, methylcellulose, hypromellose, sucrose fatty acid ester and polysorbate.

In the suspension, the dispersant may be one or two selected from polyvinyl alcohol and methylcellulose.

In the suspension, the dispersant may be polyvinyl alcohol.

In the suspension, the polyvinyl alcohol may have a saponification degree of 86.5-89.0, and a 4% aqueous solution thereof has a kinematic viscosity of 3 mm$^2$/s-55.7 mm$^2$/s at 20° C.

In the suspension, a blending amount of the dispersant may be 0.001% w/v-1.0% w/v.

The suspension may further contain a thickening agent.

In the suspension, the thickening agent may be one or two selected from xanthan gum and tragacanth powder.

In the suspension, the thickening agent may be xanthan gum.

In the suspension, a blending amount of the thickening agent may be 0.1% (w/v)-1.2% (w/v).

In the suspension, the edaravone particles in the suspension may have a D50 particle size of 10 μm-100 μm and a D90 particle size of 50 μm-300 μm.

In the suspension, a blending amount of the edaravone particles may be 0.06% w/v-36% w/v.

The suspension may further contain one or more additives selected from a sweetener, a stabilizer and a pH regulator.

The suspension may have a viscosity of 50 mPa·s-1750 mPa·s.

The suspension may have a density of 1 g/mL-1.5 g/mL.

In the suspension, an edaravone dissolution rate 30 minutes after starting the test may be 80% or more, when a dissolution test (test solution: First Solution; and paddle rotation speed: 50 rpm) is performed according to Japanese Pharmacopeia.

According to another embodiment of the present invention, a kit for preparing an edaravone suspension for human oral administration contains: (A) a solid composition containing edaravone particles; and (B) a dispersant solution.

According to yet another embodiment of the present invention, an edaravone suspension for human oral administration is characterized in that, when the suspension containing 90-120 mg of edaravone is orally administered to a human, edaravone in a plasma exhibits a mean Cmax of 500-2500 ng/mL and a mean $AUC_{0-\infty}$ of 1000-2500 h*ng/mL.

According to still another embodiment of the present invention, an edaravone suspension for human oral administration is characterized in that, when a crossover study in which the suspension containing 90-120 mg of edaravone is orally administered to a human is performed using an edaravone injection as a control drug product, a lower limit of a 90% confidence interval of a ratio of a Cmax geometric mean value with respect to the control drug product and a lower limit of a 90% confidence interval of a ratio of an $AUC_{0-\infty}$ geometric mean value with respect to the control drug product both exceed 0.8.

According to still another embodiment of the present invention, an edaravone suspension for human oral administration is characterized in that, when a crossover study in which the suspension containing 90-120 mg of edaravone is orally administered to a human is performed using an edaravone injection as a control drug product, a ratio of a Cmax geometric mean value with respect to the control drug product and a ratio of an $AUC_{0-\infty}$ geometric mean value with respect to the control drug product are both in a range of 0.8-1.25.

According to still another embodiment of the present invention, an ALS therapeutic agent is characterized in that a dose of a drug product per one oral administration is 1-20 mL and the dose contains 50-210 mg of edaravone.

According to an embodiment of the present invention, an edaravone suspension for oral administration that can reduce burden on ALS patients and caregivers and can achieve an ALS therapeutic effect equivalent to that of an injection can be provided.

Obviously, numerous modifications and variations of the present invention are possible in light of the above teachings. It is therefore to be understood that within the scope of the appended claims, the invention may be practiced otherwise than as specifically described herein.

What is claimed is:

1. An edaravone suspension for human oral administration, comprising:
    water;
    edaravone particles comprising edaravone and dispersed in the water; and
    a dispersant exhibiting a transmission scattering light intensity of 1% or more and dispersing the edaravone particles in the water such that the dispersant maintains the edaravone particles in a solid particle state in the water,
    wherein a blending amount of the dispersant is in a range of 0.001% (w/v) to 1.0% (w/v), a blending amount of the edaravone particles is in a range of 0.5% (w/v) to 36% (w/v), and when edaravone in the edaravone suspension is in a range of 90 to 120 mg, edaravone in a plasma exhibits a mean Cmax in a range of 500 to 2500 ng/mL and a mean $AUC_{0-\infty}$ in a range of 1000 to 2500 h*ng/mL when the edaravone suspension is orally administered to a human.

2. The edaravone suspension according to claim 1, wherein the dispersant is a dispersant exhibiting a contact angle of 80 degrees or less.

3. The edaravone suspension according to claim 1, further comprising a thickening agent.

4. The edaravone suspension according to claim 3, wherein the thickening agent is one or two thickening agents selected from the group consisting of xanthan gum and tragacanth powder.

5. The edaravone suspension according to claim 3, wherein the thickening agent is xanthan gum.

6. The edaravone suspension according to claim 3, wherein a blending amount of the thickening agent is in a range of 0.1% (w/v) to 1.2% (w/v).

7. The edaravone suspension according to claim 1, wherein the edaravone particles in the suspension have a D50 particle size in a range of 10 μm to 100 μm and a D90 particle size of in a range of 50 μm to 300 μm.

8. The edaravone suspension according to claim 1, wherein a blending amount of the edaravone particles is in a range of 1% (w/v) to 36% (w/v).

9. The edaravone suspension according to claim 1, further comprising at least one additive selected from the group consisting of a sweetener, a stabilizer and a pH regulator.

10. The edaravone suspension according to claim 1 having a density of in a range of 1 g/mL to 1.5 g/mL.

11. The edaravone suspension according to claim 1, wherein the suspension has an edaravone dissolution rate of 80% or more 30 minutes after starting a dissolution test according to Japanese Pharmacopeia.

12. The edaravone suspension according to claim 1, wherein when edaravone in the edaravone suspension is in a range of 90 to 120 mg, and a crossover study is performed such that the edaravone suspension is orally administered to a human and that an edaravone injection is used as a control drug product, a lower limit of a 90% confidence interval of a ratio of a Cmax geometric mean value with respect to the control drug product and a lower limit of a 90% confidence interval of a ratio of an $AUC_{0-\infty}$ geometric mean value with respect to the control drug product both exceed 0.8.

13. The edaravone suspension according to claim 1, wherein when edaravone in the edaravone suspension is in a range of 90 to 120 mg, and a crossover study is performed such that the edaravone suspension is orally administered to a human and that an edaravone injection is used as a control drug product, a ratio of a Cmax geometric mean value with respect to the control drug product and a ratio of an $AUC_{0-\infty}$ geometric mean value with respect to the control drug product are both in a range of 0.8 to 1.25.

14. An edaravone suspension for human oral administration, comprising:
    water;
    edaravone particles comprising edaravone and dispersed in the water; and
    a dispersant exhibiting a contact angle of 80 degrees or less and dispersing the edaravone particles in the water such that the dispersant maintains the edaravone particles in a solid particle state in the water,
    wherein a blending amount of the dispersant is in a range of 0.001% (w/v) to 1.0% (w/v), a blending amount of the edaravone particles is in a range of 0.5% (w/v) to 36% (w/v), and when edaravone in the edaravone suspension is in a range of 90 to 120 mg, edaravone in a plasma exhibits a mean Cmax in a range of 500 to 2500 ng/mL and a mean $AUC_{0-\infty}$ in a range of 1000 to 2500 h*ng/mL when the edaravone suspension is orally administered to a human.

15. The edaravone suspension according to claim 14, further comprising a thickening agent in a blending amount in a range of 0.1% (w/v) to 1.2% (w/v).

16. The edaravone suspension according to claim 14, wherein the thickening agent is one or two thickening agents selected from the group consisting of xanthan gum and tragacanth powder.

17. The edaravone suspension according to claim 14, wherein the edaravone particles in the suspension have a D50 particle size in a range of 10 μm to 100 μm and a D90 particle size of in a range of 50 μm to 300 μm.

18. The edaravone suspension according to claim 14, wherein a blending amount of the edaravone particles is in a range of 1% (w/v) to 36% (w/v).

19. The edaravone suspension according to claim 14, wherein when edaravone in the edaravone suspension is in a range of 90 to 120 mg, and a crossover study is performed such that the edaravone suspension is orally administered to a human and that an edaravone injection is used as a control drug product, a lower limit of a 90% confidence interval of a ratio of a Cmax geometric mean value with respect to the control drug product and a lower limit of a 90% confidence interval of a ratio of an $AUC_{0-\infty}$ geometric mean value with respect to the control drug product both exceed 0.8.

20. The edaravone suspension according to claim 14, wherein when edaravone in the edaravone suspension is in a range of 90 to 120 mg, and a crossover study is performed such that the edaravone suspension is orally administered to a human and that an edaravone injection is used as a control drug product, a ratio of a Cmax geometric mean value with respect to the control drug product and a ratio of an $AUC_{0-\infty}$ geometric mean value with respect to the control drug product are both in a range of 0.8 to 1.25.

* * * * *

UNITED STATES PATENT AND TRADEMARK OFFICE
CERTIFICATE OF CORRECTION

Page 1 of 1

PATENT NO. : 11,241,416 B2
APPLICATION NO. : 17/213501
DATED : February 8, 2022
INVENTOR(S) : Tetsuo Hayama et al.

It is certified that error appears in the above-identified patent and that said Letters Patent is hereby corrected as shown below:

In the Specification

Column 16, Line 32:
"40 mg of sodium bisulfate" should read -- 40 mg of sodium bisulfite --.

Signed and Sealed this
Twenty-fifth Day of April, 2023

Katherine Kelly Vidal
*Director of the United States Patent and Trademark Office*